US005837233A

United States Patent [19]
Granger

[11] Patent Number: 5,837,233
[45] Date of Patent: *Nov. 17, 1998

[54] METHOD FOR TREATING TUMORS

[75] Inventor: Gale A. Granger, Laguna Beach, Calif.

[73] Assignee: University Of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 616,880

[22] Filed: Mar. 15, 1996

Related U.S. Application Data

[63] Continuation-in-part of Ser. No. 406,388, Mar. 17, 1995, abandoned.

[51] Int. Cl.$^6$ .............................. A61K 48/00; C12N 5/00
[52] U.S. Cl. ........................ 424/93.1; 424/93.2; 435/375
[58] Field of Search ............................. 435/320.1, 240.2, 435/240.21; 424/93.21, 277.1, 9.1, 93.3

[56] References Cited

U.S. PATENT DOCUMENTS

| | | | |
|---|---|---|---|
| 4,038,145 | 7/1977 | Devlin | 195/103.5 |
| 4,677,056 | 6/1987 | Dupont et al. | 435/7 |
| 5,057,423 | 10/1991 | Hiserodt et al. | 435/240.23 |
| 5,308,626 | 5/1994 | Landucci et al. | 424/93 |
| 5,382,427 | 1/1995 | Plunkett et al. | 424/85.2 |
| 5,484,596 | 1/1996 | Hanna, Jr. et al. | 424/277.1 |

FOREIGN PATENT DOCUMENTS

WO 95/31107  11/1995  WIPO.

OTHER PUBLICATIONS

Bellgrau, "Induction of cytotoxic T cell precursors in vivo" *J. Exp. Med.* (1983) 157:1505–1515.

Chang et al., "Phase I clinical trial of allogeneic lymphocyte culture (cytoimplant) delivered by endoscopic ultrasound (EUS)–guided fine needle injection (FNI) in patients with advanced pancreatic carcinoma" *Castroenterology* (1997) 112(4):A546.

Fleshner et al., "Potential of allogneic Tumoricidal cytotoxic T lymphocytes in brain tumor adoptive immunotherapy" *J. Cell. Biochem.* (1990) Suppl. 0 (14 part B):95 (abstract CE 407).

Kruse et al., "Cellular therapy of brain tumors: Clinical trials" *Advances in Neuro–Oncology II*, Kornblith et al., eds., Futura Publishing Company, Inc., Armonk, NY, (1997) Chapter 22, pp. 487–504.

Kruse et al., "Development of human allogeneic CTL in an artificial system for intercavitary treatment of malignant glioma" *Proc. Amer. Assoc. Cancer Res.* (1995) 36:474 (abstract No. 2822).

Kruse et al., "Immune therapy of recurrent mailgnant gliomas: Intracavitary allogeneic cytotoxic T lymphocytes and human recombinant interleukin–2" *FASEB J.* (1996) 10(6):A1413 (abstract 2387).

Kruse et al., "Migration of activated lymphocytes when adoptively transferred into cannulated rat brain" *J. Neuroimmunol.* (1994) 55:11–21.

Kruse et al., "Artificial–capillary–system development of human alloreactive cytotoxic T–lymphocytes that lyse brain tumour" *Biotechnol. Appl. Biochem.* (1997) 25: (pre–publication copy) 9 pages total.

Kruse et al., "Analysis of interleukin 2 and various effector cell populations in adoptive immunotherapy of 9L rat gliosarcoma: Allogeneic cytotoxic T lymphocytes prevent tumor take," *Proc. Natl. Acad. Sci.*, vol. 87: 9577–9582, Dec. 1990.

Reed et al., "Allogeneic tumor–specific cytotoxic T lymphocytes" *Cancer Immunol. Immunother.* (1992) 34:349–354.

Schiltz et al., "Movement of allogeneic cytotoxic T lymphocytes (aCTL) infused into the parietal region of 9L gliosarcoma bearing brain" *Proc. Assoc. Cancer Res.* (1995) 36:458 (Abstract No. 2727).

Schlitz et al., "Treatment of 9L gliosarcoma with interferon–gamma enhances its cytolysis by alloreactive cytotoxic T lymphocytes in vitro" *FASEB J.* (1995)9(4):A1044 (abstract 6052).

Streilein et al., "Unraveling immune response" *Science* (1995)270:1158–1159.

Albright et al., "Immunogenetic control of brain tumor growth in rats" *Cancer Res.* (1977) 37:2512–2522.

Barba et al., "Intratumoral LAK cell and interleukin–2 therapy of human gliomas" *J. Neurosurg,* (1989) 70:175–182.

Cavallo et al., "Role of neutrophils and CD4+ T lymphocytes in the primary and memory response to nonimmunogenic murine mammary adenocarcinoma made immunogenic by IL–2 gene" *J. Immunol.* (1992) 149(11):3627–3635.

Colombo et al., Tumor cells engineered to produce cytokines of cofactors as cellular vaccines: Do animal studies really support clinical trials? *Cancer Immunol. Immunother.* (1995) 41:265–270.

Finke et al., "Characterization of the cytolytic activity of CD4+ and CD8+ tumor–infiltating lymphocytes in human renal cell carcinoma" *Cancer Res.* (1990) 50:2363–2370.

Hayes et al., "Recombinant interleukin–2–related intracerebral toxicity and LAK/rIL–2 therapy for brain tumors" *Lymphokine Res.* (1988) 7(3):337.

(List continued on next page.)

*Primary Examiner*—Jasemine C. Chambers, PHD.
*Assistant Examiner*—Karen M. Hauda
*Attorney, Agent, or Firm*—Morrison&Foerster LLP

[57] ABSTRACT

A method is provided for treatment of a mammalian patient having a tumor by administering to the patient allogenic donor lymphocytes that have been co-cultured in the presence of the patient-derived lymphocytes under conditions sufficient to alloactivate the donor lymphocytes. It is preferred that the donor lymphocytes be introduced intralesionally. This method is preferred for treatment of glioblastoma in humans.

37 Claims, 2 Drawing Sheets

OTHER PUBLICATIONS

Jeffes et al., "Therapy of recurrent high grade gliomas with surgery, autologous mitogen–activated IL–2–stimulated (MAK) killer lymphocytes, and rIL–2: II. Correlation of survival with MAK cell tumor necrosis factor production in vitro" *Lymphokine Cytokine Res.* (1991) 10(2):89–94.

Kondo et al., "Rationale for a novel immunotherapy of cancer with allogeneic lymphocyte infusion" *Med. Hypotheses* (1984) 15:241–277.

Kruse et al., "Systemic chemotherapy combined with local adoptive immunotherapy cures rats bearing 9L gliosarcoma" *J. Neuro–Oncol.* (1993) 15:97–112.

Kruse et al., "Intracranial administrations of single or multiple source allogeneic cytotoxic T lymphocytes: chronic therapy for primary brain tumors" *J. Neuro–Oncol.* (1994) 19:161–168.

Leshem et al., "In vitro elicitation of cytotoxic response against a nonimmunogenic murine tumor be allosensitization" *Cancer Immunol. Immunother.* (1984) 17:117–123.

Merchant et al., "Adoptive immunotherapy for recurrent glioblastoma multiforme using lymphokine activated killer cells and recombinant interleukin–2" *Cancer* (1988) 62:665–671.

Merchant et al., "Immunotherapy for malignant glioma using human recombinant interleukin–2 and activated autologous lymphocytes. A review of pre–clinical investigations" *J. Neuro–Oncol.* (1990) 8:173–188.

Mitchell et al., "Active specific immunotherapy of melanoma with allogeneic cell lysates. Rational, results, and possible mechanisms of action" *Ann. N.Y. Acad. Sci.* (1993) 690:153–166.

Naganuma et al., "Complete remission of recurrent glioblastoma multiforme following local infusions of lymphokine activated killer cells. Case report" *Acta. Neurochir.* (1989) 99:157–160.

Rosenburg et al., "A progress report on the treatment of 157 patients with advanced cancer using lymphokine–activated killer cells and interleukin–2 or high doses interleukin–2 alone" *New England Journal of Medicine*(1987) 316(15):889–897.

Strausser et al., "Lysis of human solid tumors by autologous cells sensitized in vitro to alloantigens" *J. Immunol.* (1981) 127(1):266–271.

Topalian et al., "Immunotherapy of patients with advanced cancer using tumor–infiltrating lymphocytes and recombinant interleukin–2: A pilot study" *J. Clin. Oncol.* (1988) 6(5):839–853.

Yoshida et al., "Local administration of autologous lymphokine–activated killer cells and recombinant interleukin–2 to patients with malignant brain tumors" *Cancer Res.* (1988) 48:5011–5016.

Zarling et al., "Generation of cytotoxic T lymphocytes to autologous human leukemia cells by sensitization to pooled allogeneic normal cells" *Nature* (1978) 274:269–271.

Fletcher, et al., Recent Advances in the Understanding of the Biochemistry and Clinical Pharmacology of Interleukin–2, Lymphokine Research, 1987, vol. 6, No. 1, pp. 45–57.

Carson, et al., Rat Mitogen–Stimulated Lymphokine–Activated T Killer Cells: Production and Effects on $C_6$ Glioma Cells in Vitro and In Vivo in the Brain of Wistar Rats, Journal of Immunotherapy, 1991, vol. 10, No. 2, pp. 131–140.

Ammirati et al., "Reoperation in the treatment of recurrent intracranial malignant gliomas." *Neurosurgery* (1987) 21:607–614.

Harsh et al., "Reoperation for recurrent glioblastoma and anaplastic astrocytoma." *Neurosurgery* (1987) 21:615–621.

Redd et al., "Allogeneic tumor–specific cytotoxic T lymphocytes" *Cancer Immunol. Immunother.* (1992) 34:349–354.

Schiltz et al., "Treatment of 9L gliosarcoma with interferon–gamma enhances its cytolysis by alloreactive cytotoxic T lymphocytes in vitro" *FASEB J.* (1995) 9(4):A1044 (Abstract 6052).

Wekerle., "Lymphocyte traffic to the brain" pp. 67–85 in *The Blood–Brain Barrier*, W.M. Pardridge, ed., Raven Press Ltd, NY (1993).

Zeltzer et al., "Brain tumor vaccines and artificial lymph nodes in brain tumors—fantasy or reality?" *Med. Ped. Oncol.* (1995) 25:277.

Appendix A: Curriculum vitae of Gale A. Granger.

Appendix B (item 1): E.W.B. Jeffes et al. Therapy of recurrent high grate gliomas with surgery, and autologous mitogen activated IL–2 stimulated killer (MAK) lymphocytes . . . *J. Neuro–Oncol.* 15:141–155, 1993.

Appendix B (item 2): R.S. Yamamoto et al. Basical and clinical studies with intratumor immonotherapy of gliomas with alloimmune lymphoid cells. Poster presentation, American Association of Neurological Surgeons.

Appendix B (item 3): G. Ioli et al. "Basic & clinical studies with intratumor immunotherapy of gliomas with allogeneic lymphoid cells" *Proc. Amer. Assoc. Cancer Res.* (Mar. 1994) 35:518 (Abstract 3088).

Appendix B (item 4): G. Granger et al. "Basic and clinical studies of intralesional therapy of gliomas with allogeneic lymphoid cells" *Proc. Amer. Assoc. Cancer Res.* (Mar. 1995) 36:472 (Abstract 2812).

Appendix C: Letters regarding Gifts from Good Samaritan Hospital to support research of Gale A. Granger; Table of Gifts.

Appendix D: List of patients treated according to the invention up to Sep. 26, 1996.

Appendix E: Break–down of charges for alloactivated donor cells produced at U.C.I.

Protocol 1 (item 1): Phase I trial for brain cancer, Good Samaritan Hospital. Protocol version originally filed with the IRB at the Good Samaritan Hospital.

Protocol 1 (item 2): Phase I trial for brain cancer, Good Samaritan Hospital. Protocol version as subsequently amended to cover 20 patients.

Protocol 1 (item 3): "Informed Consent Form" (Patient).

Protocol 2 (item 1): Phase I trial for brain cancer, Long Beach Memorial Hospital.

Protocol 2 (item 2): "Consent to Act as a Research Subject" (Donor).

Protocol 2 (item 3): "Consent to Act as a Research Subject" (Patient).

Protocol 3 (item 1): Phase I trial for metastatic melanoma, U.C.I. Medical Center.

Protocol 3 (item 2): "Consent to Act as a Human Research Subject" (Donor).

Protocol 3 (item 3): "Consent to Act as Human Research Subject" (Patient).

Protocol 4 (item 1): Phase I trial for pancreatic canter, U.C.I. Medical Center.

Protocol 4 (item 2): "Consent to Act as a Human Research Subject" (Patient).

Protocol 4 (item 3): "Consent to Act as a Human Research Subject" (Donor).
Protocol 5 (item 1): Phase I trial for bladder & prostate cancer, U.C.I. Medical Center.
Protocol 5 (item 2): "Consent to Act as a Human Research Subject" (Patient).
Protocol 5 (item 3): "Consent to Act as a Human Research Subject" (Donor).
Protocol 6: Phase II trial for brain cancer, Good Samaritan Hospital.
Protocol 7: Phase II trial for brain cancer, U.C.I. Medical Center.

Declaration by John C. Hiserodt regarding Human Clinical Trials.

Appendix F: Curriculum vitae of John C. Hiserodt.

Appendix G: "Immunotherapy for recurrent high grade gliomas: I. A pilot study using intratumoral implants of MLC–activated allogeneic lymphoid cells for the treatment of recurrent malignant astrocytomas" by J.C. Hiserodt, S. Jacques, C. Dumas, and G.A. Granger. [Unpublished manuscript].

METHOD FOR TREATING TUMORS

This application is a continuation-in-part of U.S. patent application Ser. No. 08/406,388, filed Mar. 17, 1995.

BACKGROUND OF THE INVENTION

1. Field of the Invention

This invention relates to methods for inhibiting tumor cell proliferation. More particularly this invention relates to a method for inhibiting tumor cell proliferation by enhancing the patient's ability to respond immunologically to the tumor.

2. Description of Related Art

Traditional therapies have done little to alter the outcome for patients with high-grade brain tumors, such as glioblastomas, and many other types of tumors, such as systemic melanoma, and cancers of the head and neck. Patients with resectable primary tumors generally experience recurrence of the tumor within one year after surgery, chemotherapy, or radiation. Often these tumors progress rapidly, with or without further conventional therapy. Thus, there is the need to develop new modes of therapy for these deadly tumors.

A new family of cancer therapies developed in recent years are based on immunotherapy. In general, tumor immunotherapies take one of two approaches: 1) various techniques are employed to activate the patient's immune system to attack the tumor; or 2) the lymphoid cells of the patient are removed and activated by in vitro techniques to produce anti-cancer activity, and the activated cells are then systemically reintroduced into the patient. The clinical effectiveness of these various types of immunotherapy are being evaluated in patients with different types of cancers. However, one of the major problems associated with both of these types of immunotherapy is toxicity observed when immunotherapeutic agents are administered systemically. A method developed to avoid this toxicity is intralesional administration of immunotherapy, for instance by injection directly into the tumor. Intralesional administration of various forms of immunotherapy to cancer patients does not cause the toxicity seen with systemic administration of immunologic agents (M. Fletcher, et al., *Lymphokine Res.* 6:45, 1987; H. Rabinowich, et al., *Cancer Res.* 47:173, 1987; S. A. Rosenberg, et al., *Science* 233:1318, 1989; and G. Pizz, et al., *Int. J. Cancer* 34:359, 1984).

Recent studies indicated that immunization of animals with tumor cells that were genetically engineered to secrete different cytokines enhanced the induction of a therapeutic immune response. The cytokines are believed to induce a complex set of reactions including: a) increased expression of tumor antigens; b) inflammation and infiltration of the tumor with host lymphoid cells; c) induction of tumor specific immunity; and d) activation of both nonspecific and specific host anti-tumor effector mechanisms, which destroy the tumor. However, although this technique may ultimately prove useful, because it is extremely costly and time consuming, its application may be limited.

Studies in experimental animals (primarily mice) show that the chronic release of cytokines within a tumor may induce a host anti-tumor response and tumor regression. Repeated intralesional injection of cytokines such as Interleukin-2 (IL-2), Tumor Necrosis Factor (TNF) and Interferon-γ (INF-γ) has been shown to cause regression of cutaneous sarcomas (S. P. Creekmore, et al., *Resident and Staff Physician* 34:23–31, 1988; P. Greenberg, et al., *Basic and Tumor Immunology* (R. Herberman, ed.) p. 302, 1983; E. Grim, et al., *Lymphokines,* 9:279–311, 1984; G. Forni, et al., *Lymphokines* 14:335–360, 1987). It has also been shown that injection into a tumor of the animal's tumor cells that have been genetically engineered to secrete cytokines such as IL-2, IL-4, TNF and Granulocyte Monocyte Colony Stimulating Factor (GM-CSF) will induce host anti-tumor immunity (E. Feron, et al., *Cell* 60, 397–403, 1990; P. Galumbek, et al., *Science* 254:713–716, 1991; A. Ascher, et al., *J. of Immunol.* 146:3227–3234, 1991). These latter results have been obtained even in treatment of tumors that were previously thought to be non-immunogenic.

J. M. Redd, et al. (*Cancer Immunology and Immunotherapy* 34(5):349, 1992) have shown in rats that allogeneic lymphocytes sensitized against donor alloantigens can inhibit tumor formation when co-injected into the brain of a rat with 9 L glioblastoma. In a separate study, both normal and alloimmune spleen cells from Wistar rats were injected into established 6-day T9 brain tumors in the Fischer rat. Intralesional injection of normal Wistar spleen cells from Wistar rats, previously immunized against Fischer alloantigens, cured the tumors in 50% of the Fischer rats. In contrast, untreated animals and non-responders died within 30 days. Survivors appeared completely normal and intracranial injections of allogeneic cells into normal rats caused no detectable change in behavior or survival over a three month period. Histopathologic examination of brains from treated tumor bearing animals revealed: a) mononuclear cell infiltration, massive tumor necrosis beginning at 2 to 4 days and total tumor destruction by 15 days; or 2) cellular infiltration, early tumor destruction and then tumor regrowth progressing to death of the animal. No damage to normal brain tissue was evident at any time in these animals. Tumor regressor animals developed systemic immunity, for they proved totally resistant to intracranial rechallenge with viable tumor. Although these results in rats are of interest, their value in reasonably predicting what would be seen in a highly unrelated species, such as a human, is highly questionable in view of the considerable species diversity which exists, especially with respect to the immunological response to tumors.

Human glioma patients with localized and surgically accessible tumors are logical candidates for intralesional immunotherapy. Multiple Phase I studies in adult patients with gliomas have been reported employing intratumor implants of autologous peripheral blood lymphocytes activated in vitro with IL-2. While little clinical effect was noted, negative side effects were few and occurred only when excessive levels of IL-2 were co-administered with the cells (K. S. Jacobs, et al., *Cancer Res.,* 47:2101, 1986; R. Merchant, et al., *Neurosurgery* 23:725, 1988). Studies of these patients revealed that survival correlated directly with the ability of implanted cells to secrete the cytokine TNF. The discovery of inhibitors for both TNF and IL-1 in the serum or tumor cyst fluid, and in primary cultures of the tumors from these patients suggests the tumor cells surround themselves with agents that block the host anti-tumor response. These inhibitors may prevent cytokine activated implanted cells from remaining active in the tumor long enough to cause its destruction. This concept is supported by findings in brain tumor studies in rats. When IL-2 active lymphoid cells were implanted into C6 and T9 glioma brain tumors in Wistar and Fischer rats, respectively, histopathologic examination revealed the implanted IL-2 activated lymphoid cells only remained in the tumor site for 4 to 6 days (W. Carson et al., *J of Immunotherapy* 10(2):131–140, 1991).

The mechanisms operative in causing tumor regression in the animals treated with allogeneic lymphoid cells include a graft vs. host and host vs. graft reaction in the tumor site. These powerful immunologic reactions may stimulate high levels of endogenous cytokine production in the tumor, overcome local levels of cytokine inhibitors, and presumably stimulate infiltration, recruitment and activation of both specific and non-specific host anti-tumor activity. The tumor regressor animals were found to be resistant to tumor rechallenge. However, it has heretofore been unknown whether any treatments based on similar methods would achieve similar results in human subjects sufficient to be considered effective in the treatment of human tumors.

Therefore, in view of the limitations of the prior art, new and better methods for treating mammalian tumors are needed. In particular, new methods of intratumor immunotherapy are needed for human cancer patients for whom regression of an individual solid tumor could prove life saving.

SUMMARY OF THE INVENTION

The present invention provides a method for inhibiting tumors in mammals. In the general practice of this invention, the tumor patient's peripheral blood mononuclear cells (PBMCs) are co-cultured in vitro to induce a mixed lymphocyte cell reaction with healthy lymphocytes derived from a normal donor, preferably an allogeneic donor. Preferably the normal lymphocytes are from a donor unrelated to the tumor patient, and preferably the normal lymphocytes are obtained by leukapheresis from whole blood. During co-culture the allogenic donor lymphocytes are specifically activated against the patients alloantigens. The mixture of live alloactivated donor and patient lymphocytes produced by mixed lymphocyte culture are referred to herein as "MLCs." The MLC activated cells produce a mixture of cytokines which have been shown to induce a primary immune response in vitro. In the treatment of glioblastoma, for instance, the patient is a human and the alloactivated lymphocytes are surgically implanted into the patient's brain at the primary tumor site, optionally together with the patient's PBMCs from the co-culture as a MLC mixture, to induce the patient's immune system to attack autologous tumor cells. In the treatment of other types of tumors, the MLCs are injected into a tumor site, site of metastases, or body cavity, such as the peritoneum. Optionally, the MLCs are administered peripherally, such as at a non-primary tumor site, in the treatment of tumors other than glioblastoma.

In one embodiment of the invention, the alloactivated donor lymphocytes obtained by co-cultivation with patient-derived lymphocytes are isolated from the MLC mixture and administered intralesionally as an implant placed directly into the tumor of a patient desiring protection against recurrence of a tumor, for instance in the proximity of a surgically debulked tumor, or desiring treatment of an inoperable tumor. Alternatively, the alloactivated donor lymphocytes can be administered peripherally in treatment of a tumor, such as at a secondary or metastatic tumor site. In another embodiment, the allogenic activated lymphocytes are co-cultivated with patient-derived lymphocytes, and the mixture of MLCs is implanted or introduced peripherally as a mixture.

A DETAILED DESCRIPTION OF THE INVENTION

The present invention provides a method for treating tumors in mammals using an allograft of donor lymphocytes that have been co-cultured in vitro in a mixed lymphocyte (MLC) reaction with the patient's mononuclear cells, preferably from peripheral blood, to activate the donor lymphocytes against antigens associated with the patient's tumor. It is believed that a graft v. host response and a host v. graft response to the allograft induce a powerful immunologic reaction in the tumor site that results in cytokine production and tissue destruction. During this reaction the host lymphoid cells identify both the graft lymphoid cells and tissue as foreign and both are inhibited or destroyed by local and systemic immune response. This host reaction occurs not only at the implant site of the graft lymphoid cells, but may also occur peripherally, such as at a secondary or metastatic tumor site. In addition, the implanted, donor lymphocytes immunologically attack the tumor in a graft v. host response. Thus, a strong immunologic reaction in the center of the tumor produces an environment that overcomes the cytokine inhibitors that may be present at the tumor site. The increase in immunologic reaction will inhibit growth, decrease size and/or eradicate established tumors or developing metastases, as well as inhibit recurrence at the site of surgically debulked tumors. Thus, the present invention provides a method for potentiating the systemic immune response to the patient's tumor by introducing into the patient a viable preparation of the alloactivated cells described herein.

Numerous studies have shown that the in vitro environment in a mixed lymphocyte reaction facilitates an active primary immune response to allogeneic and tumor associated antigens (M. Gately, et al., *JNCI* 69:1245, 1982; S. Lee, et al., *J Experimental Medicine* 147:912, 1978; J. Zarling, et al., *Nature* 262:691, 1976). In the present invention, the MLC reaction occurs within the patient's own tumor tissue, thereby stimulating the patient to respond against its own tumor. Preferably the co-culture is performed, generally from 1 to 5 days. Since release of key cytokines takes place during the early stages of the co-culture, it is preferred that the co-cultured cells be implanted in the early stages of the co-culture reaction, usually during the first 48 hours of the reaction when cytokine levels are normally highest. This method results in release of key cytokines directly into the tumor tissue so that an environment is created that is conducive to antigen recognition and development of cell mediated immunity directed against the antigen. Standard techniques, such as those based on immunoassay, can be used to measure the level of various cytokines, including TNF, LT and gamma interferon, present in the MLC culture supernatants. Levels of TNF and LT vary from 50 to 150 units of biologic activity/ml or 500 to 3500 pg/ml of supernatant. As a result of the in vitro co-culture, healthy allogeneic lymphoid cells from a donor are specifically activated against the patient's alloantigens.

The implanted cells are generally allowed to come into direct contact with tumor cells. Thus, as used herein the term "implant" and "implanted" means that the cells are placed into the patient's body as a group, optionally within a thickening matrix of coagulated serum or other suspension or gel-like substance.

Examples of tumors that can be treated by the method of this invention include the following:

Brain tumors, such as astrocytoma, oligodendroglioma, ependymoma, medulloblastomas, and PNET (Primitive Neural Ectodermal Tumor);

Pancreatic tumors, such as pancreatic ductal adenocarcinomas.

Lung tumors, such as small and large cell adenocarcinomas, squamous cell carcinoma, and bronchoalveolarcarcinoma;

Colon tumors, such as epithelial adenocarcinoma, and liver metastases of these tumors;

Liver tumors, such as hepatoma, and cholangiocarcinoma;

Breast tumors, such as ductal and lobular adenocarcinoma;

Gynecologic tumors, such as squamous and adenocarcinoma of the uterine cervix, and uterine and ovarian epithelial adenocarcinoma;

Prostate tumors, such as prostatic adenocarcinoma;

Bladder tumors, such as transitional, squamous cell carcinoma;

Tumors of the RES System, such as B and T cell lymphoma (nodular and diffuse), plasmacytoma and acute and chronic leukemia;

Skin tumors, such as malignant melanoma; and

Soft tissue tumors, such as soft tissue sarcoma and leiomyosarcoma.

In one embodiment of the method of this invention, the alloactivated donor lymphocytes are implanted at the tumor site, optionally together with the patient's PBMCs from the co-culture, to supplement and enhance the patient's immune system attack upon autologous tumor cells. For instance, in one embodiment of the invention alloactivated human donor lymphocytes obtained by co-cultivation with patient-derived PBMCs or cell lysates of PBMCs are administered intralesionally in a human, for instance as an implant placed directly into the brain of a patient desiring protection against recurrence of a glioblastoma tumor. The alloactivated donor lymphocytes can be implanted in the proximity of a surgically debulked tumor, or a tumor treated by irradiation, chemotherapy, or other appropriate techniques. In another preferred embodiment, the allogeneic activated lymphocytes are co-cultivated with patient-derived lymphocytes and the mixture of co-cultured allogeneic and autologous cells, known herein as "the MLCs," is implanted intralesionally.

The typical implant comprises a therapeutic amount of the allostimulated donor lymphocytes. As used herein the term "a therapeutic amount" means a sufficient quantity of MLCs or donor allostimulated lymphoid cells obtained from the mixed lymphocyte culture to inhibit growth, decrease the size of and/or eradicate established tumors, and/or prevent tumor recurrence at the site of a tumor that has been surgically debulked or treated with chemotherapy or irradiation. More generally, a therapeutic amount may vary with the potency of each batch of alloactivated donor cells; the amount required for the desired therapeutic or other effect, the mode of administration, i.e., whether by direct implant into a tumor or body cavity or by peripheral administration, such as intravenously; and the rate of elimination or breakdown of the MLCs by the body once implanted or administered. In accordance with conventional prudent formulating practices, a dosage near the lower end of the useful range may be employed initially and the dosage increased or decreased as indicated from the observed response, as in the routine procedure of the physician. In general, however, a unit dosage for direct implant comprises from about $2\times10^9$ to about $6\times10^9$ MLCs. For instance, it has been discovered that in the treatment of brain tumors, the upper limit of cells that can be implanted is about $6\times10^9$. Alternatively, a unit dosage for peripheral administration usually comprises from about $2\times10^9$ to about $2\times10^{10}$ MLCs.

The invention further comprises a sterile vial or other container holding a composition comprising a unit dosage of the MLCs. Typically, the vial or container will bear a label sets forth information concerning the pharmaceutical use of the composition in treating a tumor in a human, such as FDA approval for use of the composition in the treatment of a human having one or more of the tumors against which the method of treatment of the invention is effective as described herein.

Although any known method of obtaining PBMCs from a donor can be used, it is preferred to obtain approximately 150 to 300 ml of leukapheresis suspension containing the donor PBMCs, utilizing techniques of leukapheresis that are well known in the art for supportive apheresis according to the instructions of the manufacturer of the leukapheresis equipment. For instance, leukapheresis can be performed using a Cobe 2997, Cobe Spectra® (Lakewood, Colo.), Fenwall CS 3000 (Deerfield, Ill.), or Haemonetics (Braintree, Mass.) blood cell separator. Generally, a flow rate of 40 to 50 ml/min for 2 to 4 hours with lymphocyte yield of $2-4\times10^9$ can be used to process a total donor blood volume of 7,000 to 12,000 ml to yield 200 to 250 ml of leukapheresis suspension having less than 1 ml of red cells. For example, if a Cobe 2997 blood cell separator is used, the centrifuge rate is generally about 5×g, the flow rate is up to about 45 ml/min and the collection rate is no more than or equal to 2.5 ml/min. One skilled in the art will appreciate that the yield of lymphocytes will vary with the donor and the leukapheresis machine used. For instance, if the donor pre-absolute lymphocyte counts are in the $0.6\times10^9$ to $1.0\times10^9$ level, as little as 150 ml of donor leukapheresis suspension can be drawn.

If desired, the donor cells can be contacted with a stimulatory cytokine such as IL-2 to trigger activation of the cells to the patient-derived antigen during co-culture and to further stimulate lymphocyte proliferation.

Donor PBMCs are obtained from the donor blood fraction, exercising care to avoid rupture of mononuclear cells, for instance by centrifuging the blood fraction containing the mononuclear cells through a cell separation medium such as Histopaque® 1.077 at 350×g for 7 to 10 minutes. Those of skill in the art will know of other PBMC cell separation techniques that can readily be utilized. Donor blood is typically pre-screened 3-7 days prior to surgery for HIV, Hepatitis A, B, and C, and VDRL.

Sufficient anticoagulant, such as 2% citrate, is added to the donor and patient blood or blood fraction to prevent coagulation upon withdrawal. Alternative anticoagulants and mixtures thereof known to one of skill in the art can also be used, such as anti-coagulant citrate dextrose formula A (ACDA) 15 mi/citrate 100 ml; anti-coagulant citrate dextrose formula B (ACDB) 25 ml/citrate 100 ml; or citrate phosphate dextrose (CPD) 14 ml/citrate 100 ml.

Typically, whole blood is withdrawn from the patient to be treated according to the invention using methods known in the art, such as vena puncture. PBMCs are isolated from patient whole blood, usually by centrifugation through a cell separation medium, such as Histopaque® 1.077 (Sigma, St. Louis, Mo.), and are thoroughly washed to free the cells of the clotting factor in the patient's blood.

Samples of both the donor's and patient's blood or blood fraction should be thoroughly tested to ensure sterility before co-culturing of the cells. Typical of the tests for sterility of blood components that can be conducted by one of skill in the art are those using such growth media as thioglycollate broth, tryptic soy broth and Roswell Park Memorial Institute Tissue Culture Medium (RPMI) with 10% heat-inactivated fetal bovine serum (FBS)(RPMI-10%) and 1% L-glutamine with no added antibiotics. Sterility tests utilizing the culture of blood cells in such growth media are illustrated in Example 1 of this application. Alternative sterility tests will be known to those of skill in the art.

Before mixed lymphocyte culture can be performed, typically the PBMCs isolated from whole blood are analyzed to determine the number of live cells per unit volume. This can be performed, for example, by using a stain that differentiates between living and dead cells and counting the cells in a Neubauer chamber. Typical stains for this use are trypan blue and Eosin Y dyes, both of which can be used in wet preparations. Alternative stains will be known to those of skill in the art. Generally, the concentration of live cells is standardized by diluting the preparation of PBMCs to achieve a predetermined concentration of live cells per unit volume. Although one skilled in the art may select a number somewhat higher or lower, it is generally preferred that the number of live cells be fixed at a concentration of about $10^7$ cells/ml for the purposes of conducting the mixed lymphocyte culture. The donor cells are typically cultured at a ratio of 10:1 to 20:1 compared to patient cells.

Standard techniques for conducting mixed lymphocyte culture using mammalian (i.e., human) cells are well known in the art and are illustrated in Example 1 of this application. See, for instance, *Current Protocols in Immunology,* Ed. J. E. Coligan, et al., John Wiley & Sons, Inc., 1994, Sec. 7.10 and M. Gately, et al., supra; S. Lee, et al., supra; and J. Zarling, et al., supra, which are incorporated herein by reference in their entirety. To block response of the patient stimulator cells to the donor responder cells (back stimulation), it is preferred that the patient cells be irradiated or treated with a DNA binding agent, such as mitomycin C, before mixture of the cells during co-culture to reduce or eliminate patient cell proliferative potential, as is well known in the art. In the present invention, donor lymphocytic cells are typically co-cultured in a short term mixed lymphocyte culture with the patient's PBMCs for a period of at least 48 hours, and preferably from 1 to 5 days. As a result of the in vitro co-culture, healthy lymphoid cells from the unrelated donor are specifically activated against the patient's tumor associated antigens.

Preparations for parenteral or intravenous administration are typically contained in a "physiologically compatible carrier." Since the cells utilized in the practice of this invention are live, a physiologically compatible carrier is one that does not impair viability of the cells, i.e., is hypotonic and at physiological pH. Such carriers include sterile aqueous salt solutions, suspensions and emulsions, including saline and buffered media, Ringer's dextrose, dextrose and sodium chloride, and lactated Ringer's solution. Intravenous vehicles include fluid and nutrient replenishers, electrolyte replenishers, such as those based on Ringer's dextrose, and the like. For administration by non-intravenous routes, the carrier can be in the form of clotted plasma, preferably the patient's clotted plasma. Alternatively the carrier can be a plasma-free, physiologically compatible, biodegradable solid or semi-solid, such as a gel, suspension or water soluble jelly. Acacia, methylcellulose and other cellulose derivatives, sodium alginate and tragacanth suspensions or gels are suitable for use as carriers in the practice of this invention, for example, sodium carboxymethylcellulose 2.5%, tragacanth 1.25% and guar gum 0.5%.

In a preferred method of implant at a tumor site, the co-cultured lymphocytes are collected from the co-culture supernatant (after at least 48 hours of co-culture) by centrifugation at the time of surgery. The collected cells are washed two times with injectable saline and re-suspended in platelet free, decalcified plasma obtained from the patient the previous day. The cells in plasma are transported to surgery, the plasma is re-calcified by the addition of calcium, preferably in the form of calcium gluconate so that the plasma clots, embedding the cells in an autologous plasma clot. The patient's tumor is then surgically debulked, and the clot is aseptically minced and implanted into the tumor site.

The following examples illustrate the manner in which the invention can be practiced. It is understood, however, that the examples are for the purpose of illustration and the invention is not to be regarded as limited to any of the specific materials or conditions therein.

EXAMPLE 1

A. Mixed Lymphocyte Cell (MLC) Culture Procedure 1. Collection of responder PBMC from unrelated donor.

Peripheral blood mononuclear cells (PBMCs) were collected by leukapheresis from normal healthy donors unrelated to the patient. Donors were pre-screened to test for complete blood count (CBC) with differential, Hepatitis A, B, and C, VDRL, and HIV-I.

Approximately 150 to 300 ml of leukapheresis suspension containing PBMC was collected from each donor, using standard blood donation procedures for supportive apheresis according to the manufacturers' instructions. The leukapheresis was performed using a Fenwall CS 3000 (Deerfield, Ill.) blood cell separator. A flow rate of 40 to 50 ml/min for 2 to 4 hours with lymphocyte yield of 2–4×$10^9$ processed a total donor blood volume of 7,000 to 12,000 ml to yield 200 to 250 ml of leukapheresis suspension having less than 1 ml of red cells. If a Cobe 2997 blood cell separator was used, the centrifuge rate was 5×g, the flow rate was up to 45 ml/min, and the collection rate was no more than or equal to 2.5 ml/min.

However, if donor pre-absolute lymphocyte counts were in the 0.6×$10^9$ to 1.0×$10^9$ range, as little as 150 ml of leukapheresis product was drawn. Hematocrit for the final product was 3.5%. At least one total blood volume was processed for 80% efficiency of lymphocyte collection.

The anticoagulant used was either 2% citrate or a citrate/anticoagulant ratio of ACDA-15 ml/citrate-100 ml; ACDB-25 ml/citrate-100 ml; or CPD-14 ml/citrate-100 ml. To obtain the utmost product purity, the actual and final product from the cell separator was transported as a pure concentrate of cells in autologous plasma. The cells were not washed, and no albumin was added.

2. Preparation of donor cells.

The leukapheresis product was transported to the MC Oncology Research Laboratory for the production of allogeneic mixed lymphocyte cells (MLCs) for immunotherapy.

Cells were drained from the leukapheresis pack into two or three 250 ml centrifuge tubes, removing and setting aside 3 ml for sterility tests to be done during centrifugation. Cell concentrate was diluted with phosphate buffered saline (PBS) and centrifuged for 7 minutes at 2,000 rpm. Centrifugation was repeated twice for a total of three times to wash the cells free of the clotting factor in the donor's serum.

Three 1 ml aliquots from the 3 ml removed from the leukocyte suspension were placed into sterile capped tubes for sterility testing. The first 1 ml aliquot was added to thioglycollate medium (Difco, Detroit, Mich.) (30°–35° C., 48 hr.); a second 1 ml was added to tryptic soy broth (Difco, Detroit, Mich.) (25°–30° C., 48 hr.); and the third 1 ml was added to RPMI 1640 (GIBCO, Gaithersburg, Md.) with 10% heat-inactivated FBS (RPMI-10%) and 1% L-glutamine, but without antibiotics.

Cells were spin washed twice at 150 g for 10 minutes in PBS to remove platelets. The supernatant was very carefully discarded as cells were in a slurry and not a pellet. Cells were resuspended in AIM V (GIBCO, Gaithersburg, Md.) supplemented with 2% heat inactivated FBS (2% AIM V) to 420 ml, and placed into a T-175 cm$^2$ flask.

Patient or donor blood was diluted 1:1 with sterile saline. For cell separation, 35 ml of cell suspension was carefully layered onto 15 ml Histopaque® 1.077 suspension medium (Sigma, St. Louis, Mo.) in each 50 ml tube and centrifuged at 250 g for 45 minutes. Centrifugation was started slowly and gradually increased to full speed. After centrifugation, the interface containing mononuclear cells between the Histopaque® suspension medium and the plasma layer was carefully collected with a 25 ml sterile pipet, deposited into clean 50 ml centrifuge tubes, diluted with 2% AIM V Media 1:1, and centrifuged at 550 g for 7 to 10 minutes to form a cell pellet. Cells remained a minimum of time in the Histopaque® suspension medium, because it is toxic to the cells.

The supernatant was discarded, the pellet was resuspended in 2% AIM V and divided into two 50 ml centrifuge tubes to a total volume 40 ml, and centrifuged at 550 g for 5 minutes. After washing, the supernatant was discarded. The washing step was repeated twice for a total of three times. After the last wash, cells in each tube were resuspended in 50 ml of 2% AIM V. Aliquots of 1 ml of the resuspended cells were diluted to a ratio of 1:10 in 2% AIM V per tube, then further diluted 1:1 in Trypan Blue (Sigma, St. Louis, Mo.) to distinguish dead from live cells, and the live cells were counted in a hemocytometer. Cells were set at $2 \times 10^6$/ml with 2% AIM V.

3. Collection of stimulator PBMC from tumor patients.

From 200 to 400 ml of peripheral blood cells were drawn from each glioblastoma patient by vena puncture and placed into 250 ml centrifuge tubes, removing and setting aside 3 ml for sterility tests to be done during spinning. Blood cells in the centrifuge tubes were diluted with saline and centrifuged for 7 minutes at 550 g. Centrifugation was repeated twice for a total of three times to wash the cells free of the clotting factor in the patient's serum. Sterility testing was conducted as described above.

Cells were washed twice by centrifugation at 150 g for 10 minutes in saline to remove platelets, the supernatant was very carefully discarded, and 420 ml of cells were resuspended in a T-175 cm$^2$ flask in saline.

15 ml of Histopaque® 1.077 cell separation medium was added to twelve 50 ml centrifuge tubes, and 35 ml of cells suspended in saline were layered onto the Histopaque® 1.077 in each 50 ml tube. The cell suspensions were spun at 250 g for 45 minutes, starting centrifugation slowly and gradually increasing speed.

After centrifugation, the mononuclear cells at the interface between the Histopaque® cell separation medium and the plasma layer were carefully collected with a 25 ml sterile pipet into 2 sterile 250 ml centrifuge tubes and diluted with 2% AIM-V to a final volume of 250 ml. The diluted mononuclear cells were centrifuged at 550 g for 7 to 10 minutes. For washing, the supernatant was discarded, then the cell pellet was re-suspended with 2% AIM V and centrifuged at 550 g for 5 minutes. The washing step was repeated for a total of three times.

After the last washing step, cells were re-suspended in 50 ml of 2% AIM V, 1 ml of the cell suspension was diluted 1:10 in 2% AIM-V per tube, and the number of viable cells was determined by enumeration in a 1:1 in Trypan Blue as described above.

The above-described procedures for collection of cells and proof of sterility have been approved by the State of California for GMP for sterility and quality control.

4. Alloactivation of patient mononuclear cells (PBMC) with donor leukocytes.

The isolated patient PBMCs were re-suspended at $10^7$ cells/ml in AIM-V, 50 μg Mitomycin C (Bristol-Mayer Squibb, Princeton, N.J.) were added per ml of patient cell suspension, and the suspension of PBMCs was incubated at 37° C. for one hour to block response of the stimulator cells to the responder cells (back stimulation). After one hour of incubation, the excess mitomycin C was washed from the cells by alternate centrifugation (250 g for 5 min), and the cells were resuspended in AIM-V. After mitomycin treatment of the patient's PBMCs, the cells were added at a 20:1 to 10:1 donor:patient cell ratio to the donor culture (obtained as described above).

For co-culture, the donor and mitomycin C-treated patient PBMC suspension was placed in a sealed sterile Fenwal tissue culture system especially designed for culture of PBMC for reimplantation into patients. Cells were passed in sealed systems via Fenwal cell transfer units and pumps according to the manufacturers instructions, and cultured in a 37° C. incubator for 48 hours.

5. Sterility testing of alloactivated cells.

Two days prior to implantation of the cell suspension, the following three sterility tests were performed. 10 ml sterile aliquots were removed from each tissue culture bag, placed into sterile capped 15 ml centrifuge tubes, and centrifuged for 10 minutes at 450 g. In each tube, the pellet was resuspended in 3.0 ml of PBS. A 1 ml aliquot of the cell suspension was added to each of three sterile capped tubes containing 2 ml of thioglycollate broth, tryptic soy broth, or RPMI-10% and incubated for 48 hours. Each cell suspension was examined microscopically prior to implant to detect signs of microbial growth.

On the day of surgery, the cells were centrifuged out of their medium, washed two times with saline and re-suspended in platelet free, decalcified plasma obtained from the patient the previous day. The cells were transported to the operating room in plasma, then the plasma was re-calcified by the addition of calcium gluconate so that it clots just before implantation into the tumor bed.

The day of surgery a drop of collected cell pellet was again examined for sterility under the microscope. Just prior to clotting, a 100 μl aliquot of the cell suspension was added to 2 ml each of RPMI-10% without antibiotics, thioglycollate and tryptic soy broth in a sterile capped tube. The samples were then incubated for four days after surgery, and a running log was kept of this last sterility test.

Cyto-implants produced by the above described method have received FDA approval for use in human cancer patients (IND-BB 6288).

B. Intralesional implant of mixed lymphocyte cell culture.

A human Phase I trial was initiated to test the effects of intracranial injection of alloactivated allogeneic lymphoid cells in patients with recurrent glioblastoma. A total of 9 patients with recurrent Grade 3 and Grade 4 glioblastoma were entered into this trial. MLCs obtained from mixed lymphocyte culture in Step 3 above were implanted intralesionally in the debulked tumor at the time of surgery. Three patients were tested at each of three cell doses of $2 \times 10^9$, $4 \times 10^9$, and $6 \times 10^9$ of MLCs. The patients were followed clinically and magnetic resonance imaging (MRI) scans were performed at various monthly intervals on each patient following implantation to monitor the progress of the disease.

Figure 1:
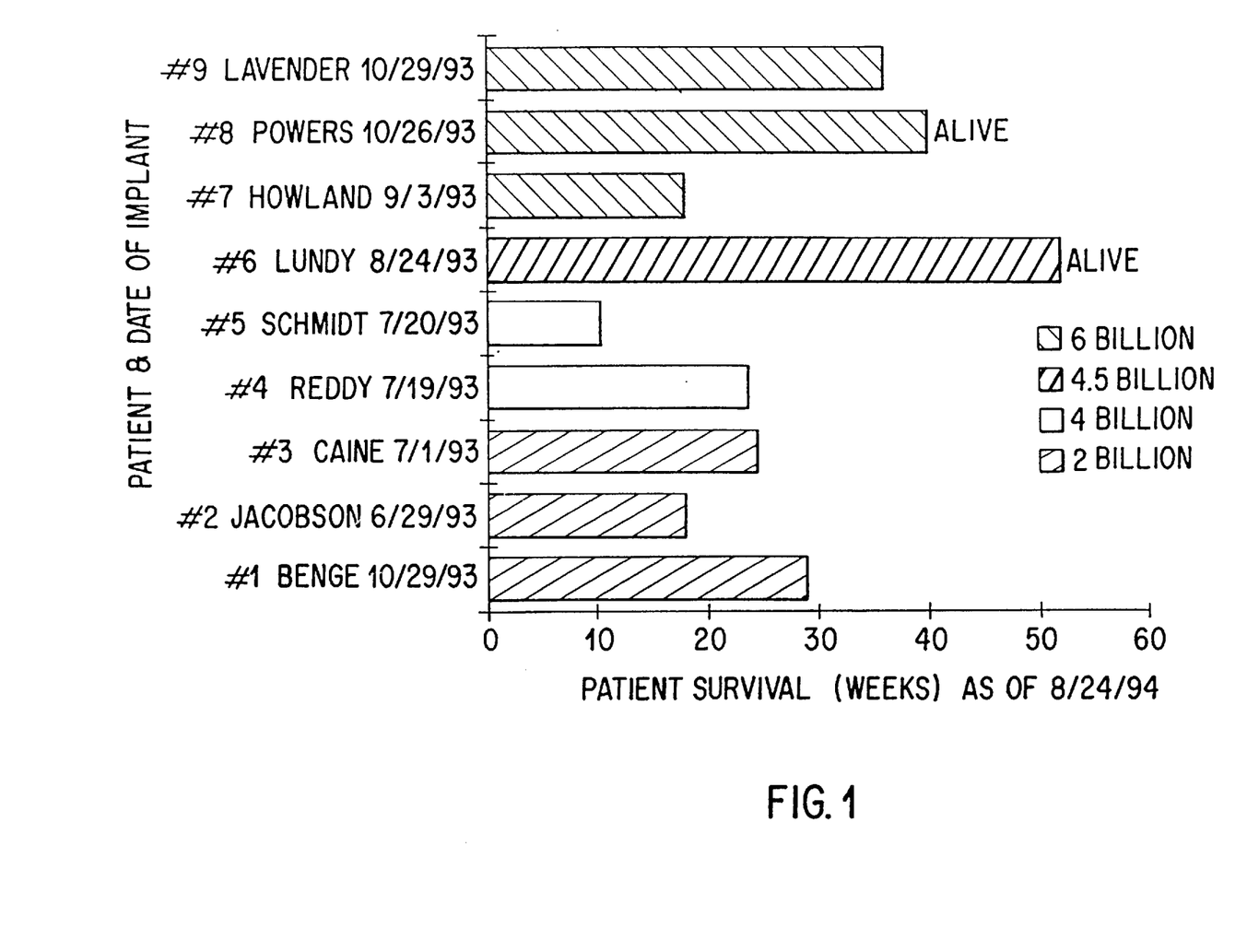
FIG. 1 shows survival times of glioblastoma patients treated with intratumor implant of MLC cells.
Figure 2:
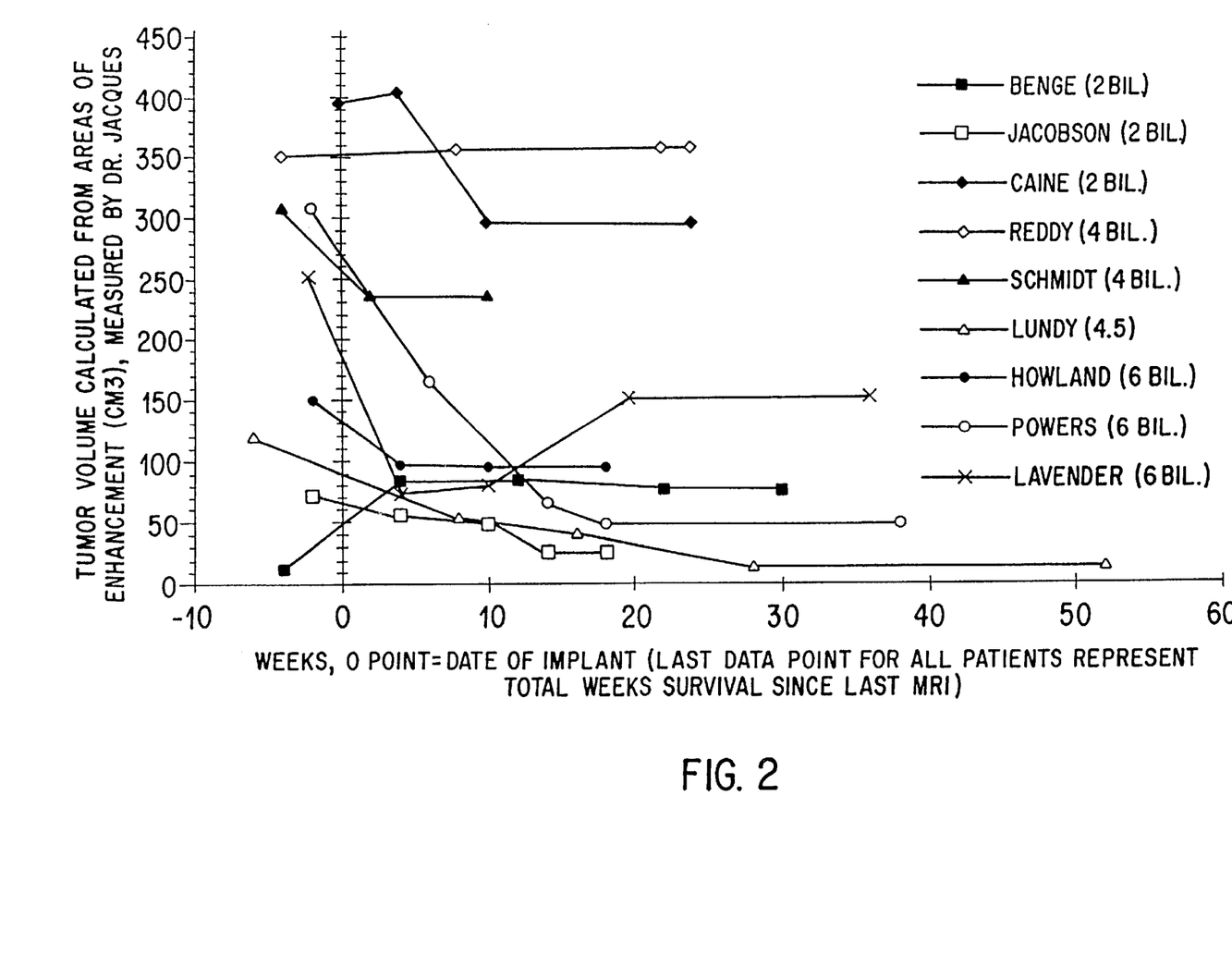
FIG. 2 is a graph showing MRI scans indicating the reduction in tumor size in nine glioblastoma patients, two patients, one receiving a single implant dose of $4 \times 10^9$ MLCs and one receiving a single implant dose of $6 \times 10^9$ MLCs, have continued to date to show a progressive reduction in tumor mass over periods of 58 and 74 weeks, respectively.

All patients complained of headache and nausea for 1 to 2 months after surgery. Patients receiving the highest cell dose experienced the highest number of symptoms. Four of the five patients, including all those in the highest dose and one each in the lower doses, showed a 50% or greater reduction in the area of tumor enhancement in MRI scans over a 1 to 3 month period after the implant. The results of MRI scans are shown in FIG. 1, which measures survival time of glioblastoma patients treated with intratumor implants of MLC cells. Two patients, one receiving a single implant dose of $4 \times 10^9$ MLCs and one receiving a single implant dose of $6 \times 10^9$ MLCs, have continued to date to show a progressive reduction in tumor mass over periods of 58 and 74 weeks, respectively. These two patients also have shown a marked improvement in Karnofsky score. The results of MRI scans are shown in FIG. 2, which measures the reduction of tumor volume as a function of time since implant of MLCs.

EXAMPLE 2

Phase I studies have been conducted in two patients with systemic melanoma. Mixed cultures of patient and donor lymphocytes were prepared as described in Example 1. The patients were treated by intralesional injection of $2 \times 10^9$ MLC cells into cutaneous tumors. Neither patient exhibited negative effects. The first patient experienced necrosis and destruction of the injected cutaneous tumor and inflammation at a distant metastasis. The second patient showed inflammation at the injected tumor, but no necrosis at the present dosage level. Treatment of these patients is ongoing.

EXAMPLE 3

A human Phase I clinical study has been conducted to test the effect of intratumor implant of MLC cells in patients with pancreatic cancer. Four patients with incurable, untreatable pancreatic cancer received intralesional implant of $4 \times 10^9$ MLC cells. Little or no toxicity was found. A reduction in tumor mass occurred and extension of life span has been observed. Three patients have experienced a greater than 50 percent reduction in tumor mass. In patient No. 3, the serum levels of CA-19-9, a marker for this tumor, declined from a high of 206 to 86 over a two month period. Seven months after treatment, two of the treated patients have returned to their jobs, have no clinical symptoms of tumor, and are living a totally normal life.

The foregoing description of the invention is exemplary for purposes of illustration and explanation. It should be understood that various modifications can be made without departing from the spirit and scope of the invention. Accordingly, the following claims are intended to be interpreted to embrace all such modifications.

I claim:

1. A method of treating a human patient having a tumor, comprising implanting at or around the site of a solid tumor in said patient, a cell population comprising alloactivated human donor lymphocytes, wherein said alloactivated human donor lymphocytes are produced by coculturing human donor lymphocytes ex vivo with leukocytes from said human patient, and wherein the implanted cell population induces the human patient to generate a therapeutic response against tumor growth.

2. A method of treating a human patient having a tumor, comprising implanting at or around the site of a solid tumor in said patient, a cell population comprising alloactivated human donor lymphocytes, wherein said alloactivated human donor lymphocytes are produced by coculturing human donor lymphocytes ex vivo with leukocytes from said human patient, and wherein the implanted cell population induces the human patient to generate a therapeutic tumor specific immune response.

3. The method of claim 1, wherein the tumor is a neuronally derived cancer.

4. The method of claim 3, wherein the tumor is a glioblastoma.

5. The method of claim 1, wherein the tumor is an epidermally derived cancer.

6. The method of claim 5, wherein the tumor is a melanoma.

7. The method of claim 1, wherein the tumor is a pancreatic cancer.

8. The method of claim 7, wherein the tumor is a pancreatic ductal adenocarcinoma.

9. The method of claim 1, wherein the tumor is a cancer selected from the group consisting of liver cancer, colon cancer, prostate cancer, and breast cancer.

10. The method of claim 1, wherein the tumor is a primary tumor.

11. The method of claim 1, wherein the tumor is a secondary or metastatic tumor.

12. The method of claim 1, wherein the implanting comprises administering the alloactivated cell population into the tumor.

13. The method of claim 1, further comprising surgically debulking the solid tumor before implanting the lymphocytes.

14. The method of claim 13, wherein the implanting comprises administering the alloactivated cell population to the bed of the debulked solid tumor mass.

15. The method of claim 1, wherein the implanted cell population comprises about $2 \times 10^9$ to $6 \times 10^9$ co-cultured cells.

16. The method of claim 1, wherein the implanted cell population comprises about $2 \times 10^9$ to $2 \times 10^{10}$ co-cultured cells.

17. A method of treating a tumor in a human patient, comprising the steps of:
   a) collecting leukocytes from the patient;
   b) collecting lymphocytes from a human donor who is allogeneic to the patient;
   c) co-culturing the donor lymphocytes with the patient leukocytes ex vivo so as to alloactivate the donor lymphocytes; and
   d) implanting a cell population comprising the alloactivated donor lymphocytes into the patient at or around the site of a solid mass of the tumor, wherein the implanted cell population induces the human patient to generate a therapeutic response against tumor growth.

18. The method of claim 17, further comprising a step of blocking proliferation of the patient leukocytes before the co-culturing.

19. The method of claim 18, wherein proliferation of the leukocytes is blocked by irradiating them or treating them with mitomycin C.

20. The method of claim 17, wherein the co-culturing is for about 48 hours.

21. The method of claim 17, wherein the tumor is a neuronally derived cancer.

22. The method of claim 21, wherein the tumor is a glioblastoma.

23. The method of claim 17, wherein the tumor is an epidermally derived cancer.

24. The method of claim 23, wherein the tumor is a melanoma.

25. The method of claim 17, wherein the tumor is a pancreatic cancer.

26. The method of claim 25, wherein the tumor is a pancreatic ductal adenocarcinoma.

27. The method of claim 17, wherein the tumor is a cancer selected from the group consisting of liver cancer, colon cancer, prostate cancer, and breast cancer.

28. A pharmaceutical composition for treating a human patient having a tumor comprising alloactivated human donor lymphocytes, wherein said alloactivated human donor lymphocytes are produced by coculturing human donor lymphocytes ex vivo with leukocytes from said human patient at a ratio of donor lymphocytes:patient leukocytes of between about 10:1 and 20:1, and wherein the pharmaceutical composition, upon administration to said human patient, induces the human patient to generate a therapeutic response against tumor growth.

29. The composition of claim 28, wherein the pharmaceutical composition comprises about $2 \times 10^9$ to about $6 \times 10^9$ of the co-cultured cells.

30. The composition of claim 28, wherein the pharmaceutical composition comprises about $2 \times 10^9$ to about $2 \times 10^{10}$ of the co-cultured cells.

31. A kit for use in treating a solid tumor in a human patient, comprising the pharmaceutical composition of claim 28 in a sterile vial.

32. A method for preparing a therapeutic composition for treating a human patient having a tumor, comprising coculturing human donor lymphocytes ex vivo with leukocytes from said human patient at a ratio of donor lymphocytes::patient leukocytes of between about 10:1 to 20:1, wherein said co-culturing produces an alloactivated cell population which, upon administration to said human patient, induces said human patient to generate a therapeutic response against tumor growth.

33. The method of claim 32, further comprising a step of blocking proliferation of the patient leukocytes before co-culturing the donor lymphocytes with the patient leukocytes.

34. The method of claim 32, further comprising testing the sterility of the therapeutic composition.

35. The method of claim 32, further comprising packaging the therapeutic composition in a sterile vial.

36. A method for inducing a therapeutic immune response in a human patient having a tumor, comprising implanting in the patient at or around the site of a solid tumor a cell population comprising alloactivated human donor lymphocytes, wherein said alloactivated human donor lymphocytes are produced by coculturing human donor lymphocytes ex vivo with leukocytes from said human patient, and wherein the implanted cell population induces the human patient to generate a therapeutic tumor specific immune response.

37. The method of claim 36, wherein the solid tumor is selected from the group consisting of glioblastoma, melanoma, pancreatic cancer, liver cancer, colon cancer, prostate cancer, and breast cancer.

* * * * *